(12) United States Patent
Payne et al.

(10) Patent No.: US 6,970,248 B1
(45) Date of Patent: Nov. 29, 2005

(54) METHOD FOR THE DETECTION OF PRODUCT TRANSITIONS IN LIQUID PIPING SYSTEMS

(75) Inventors: Fred A. Payne, Lexington, KY (US); Mary-Grace D. Danao, Lexington, KY (US)

(73) Assignee: Reflectronics, Incorporated, Lexington, KY (US)

( * ) Notice: Subject to any disclaimer, the term of this patent is extended or adjusted under 35 U.S.C. 154(b) by 284 days.

(21) Appl. No.: 10/440,382

(22) Filed: May 17, 2003

Related U.S. Application Data

(60) Provisional application No. 60/381,413, filed on May 17, 2002.

(51) Int. Cl.[7] ............................................. G01N 21/00
(52) U.S. Cl. ..................................... 356/436; 356/442
(58) Field of Search ............................... 356/436–442, 356/337, 338; 73/61.48

(56) References Cited

U.S. PATENT DOCUMENTS

| | | | |
|---|---|---|---|
| 5,172,193 A | * | 12/1992 | Payne et al. ................ 356/445 |
| 5,984,262 A | * | 11/1999 | Parsons et al. ......... 251/129.04 |
| 6,507,401 B1 | * | 1/2003 | Turner et al. ................ 356/436 |
| 6,831,741 B1 | * | 12/2004 | De Kruif et al. ........... 356/338 |

OTHER PUBLICATIONS

M. C. Danao, F. A. Payne, "Determining Product Transitions in a Liquid Piping System Using a Transmission Sensor," Transactions of the ASAE, 2003 American Society of Agricultural Engineers, vol. 46(2): 415-421.
Fred A. Payne, "Optical Sensors for Monotring Coagulation, Particulates and Performance of Separators," Cheeseworks, Quarterly Newsletter of the Australian Cheese Technology Program, vol. 4, No. 3 2000.

* cited by examiner

*Primary Examiner*—Layla G. Lauchman
(74) *Attorney, Agent, or Firm*—King & Schickli, PLLC

(57) ABSTRACT

A method for detecting a characteristic of a flow of a liquid in a pipe for intended use in determining a transition among or between two products forming the flow is disclosed. The method may comprise obtaining a first signal representative of the characteristic of the flow, determining when a substantial change in the characteristic is occurring; determining the transition point, and determining a transition time for the substantial completion of the transition based on parameter(s) generated from the first signal.

26 Claims, 12 Drawing Sheets

METHOD FOR THE DETECTION OF PRODUCT TRANSITIONS IN LIQUID PIPING SYSTEMS

This application claims the benefit of U.S. Provisional Patent Application Ser. No. 60/381,413, filed May 17, 2002, the disclosure of which is incorporated herein by reference.

TECHNICAL FIELD

The present invention relates generally to a method for detecting a change from one product to another in a liquid piping system and more, particularly, to a method for establishing the transition point and estimating the transition time between two liquid products of different physical or optical properties.

BACKGROUND OF THE INVENTION

Transition sensing is one of the many sensor applications needed for automating food processing plants. Transition sensors determine the change from one product to another in a liquid piping system. Transition sensors that accurately determine the interface between product changes allow for more accurate control over processes to ensure product quality, reduced waste in food processing plants, and increased food safety. For example, in a typical pasteurization system, water is re-circulated through the pasteurizer while the temperature is rising to the pasteurization temperature. Once the desired temperature is reached, operators manually divert the flow of water to a drain line and open a valve to allow raw milk to chase the water through the pasteurizer. Operators use stopwatches to determine the time it takes for all the water to pass through the system. At the end of the "specified time", they divert the fluid flow from the drain line to the process line. The "specified time" is not always accurate and the operators are occasionally late in manually diverting the product, resulting in product loss and an increase in effluent loading.

Optical sensors are currently commercially available for this application but are limited because they typically operate for only one product and require calibration to this product in the plant. The currently available sensors are response-based transition sensors, i.e., the output signal is proportional to an optical response (reflectance or transmission), and the sensor output is based on the detection of a specific level of reflectance or transmission. These sensors require calibration in a food processing facility for operation. Response-based sensors are generally unsatisfactory for operations involving multiple products where the optical or physical properties differ significantly. A single response-based transition sensor has difficulty establishing process control set points for two optically different (e.g., high vs. low reflectance) fluids. Recalibration is required if the response of a product changes due to changes in fat/protein/sugar content of the liquid, aging of the light source, scratch on lenses, etc. The plant technical personnel must be keenly aware of these changes to keep the sensors operating properly.

A versatile time-based method was developed for use with an optical transmission sensor. This sensor system performs for multiple products and does not require plant calibration. This disclosure is based on the application of the developed method to a measured optical sensor. It should be apparent that the method could be applied to the measured response of other sensors such as conductivity, temperature, ionic strength, pH, refraction, sonic properties, etc. This technology can be applied for monitoring the fluid pipe flows in the food, beverage, dairy, bioprocess, and chemical process industries among others.

DEFINITIONS

1. Transition point is the inflection point of the transition period as described by G and R, or the point when the absolute value of the first derivative of R is at its maximum, or the point when the second derivative of R is zero.
2. Transition time is defined as the time required to pass from 95% to 5% of the product in the mixture.
3. Stationary period is the period of time when the change in light transmission through a fluid with respect to time is not significantly different from zero.
4. Transition period is defined as the time when the change in the light transmission through a fluid with respect to time is different from zero.
5. Threshold value is the value of the threshold function H that is considered a significant change in optical transmission.

NOMENCLATURE $\beta_1$, $\beta_2$ regression coefficients.
$D_R$ number of data points collected in one second.
$\Delta t_{12}$ time elapsed between the maxima of the first and second derivatives.
$\Delta t_{delay}$ total time delay resulting from smoothing function, derivative functions, and LOGIC conditions.
F the measured optical response of light transmission through a distance of the product and generally measured in pulses/second or Hz.
G the logarithm transformation of the measured optical response, G= ln (F), which transforms the signal to one proportional to concentration.
H the threshold function or the normalized percent change in measured light transmission.
i index used in summation of data points for averaging.
$\mu$ product viscosity in Pascal-second.
L pipe system length measured in meters.
n index of data points with the most recent point collected being equal to 1, and the next more recent, 2, and so forth.
$N_D$ required number of data points to determine whether the maximum of the first derivative curve has passed.
$N_F$ required number of data points to calculate the first derivative.
$N_H$ number of data points in the Head period of the R calculation.
$N_S$ required number of data points to calculate the second derivative.
$N_T$ number of data points in the Tail period of the R calculation.
$N_W$ number of data points in the Wait period of the R calculation.
$N_X$ required number of data points to perform the averaging calculations.
$\rho$ product density in kilograms per cubic meter.
R smoothened response obtained by a smoothing procedure operating on G and resulting in a smooth sigmoidal curve representing the transition period.
R' the first derivative of R obtained by a first derivative smoothing procedure operating on R.
R" the second derivative of R obtained by a second derivative smoothing procedure operating on R'.

$S_H$ average of the Head points used in the smoothing procedure operating on G.

$S_T$ average of the Tail points used in the smoothing procedure operating on G.

$S_{1H}$ average of the Head data points of R used in the first derivative procedure.

$S_{1T}$ average of the Tail data points of R used in the first derivative procedure.

$S_{2H}$ average of the Head data points of R' used in the second derivative procedure.

$S_{2T}$ average of the Tail data points of R' used in the first derivative procedure.

$t_{est}$ estimated transition time in seconds.

$t_{meas}$ measured transition time in seconds.

v process velocity measured in meters per second.

SUMMARY OF THE INVENTION

One objective of the present invention is to develop an intelligent transition sensor system that eliminates the requirement for in-plant calibration and distinguishes between any two products of different optical properties in a liquid piping system. The intelligent transition sensor system developed includes (a) a fiber optic sensor in transmission configuration to provide real-time measurement of the light transmission through the liquid being processed and (b) a robust method for detecting the transition point and estimating the transition time. The example used to illustrate the performance of the method described in this disclosure is based on a data collection rate of ten measurements (data points) per second and on typical pipe flow conditions encountered in the dairy industry.

A method for detecting product transitions includes the following steps:
1. Directing light from a light source toward the liquid product in a piping system.
2. Sensing the transmission of that light through the liquid product.
3. Analyzing the sensed light transmission profile using a method based on derivative analysis to determine the following:
   a. transition point, and
   b. transition time.
4. Sending an output signal to indicate the location of the transition point.
5. Sending an output signal to indicate the transition time.

The light transmission profile can be divided into two periods—stationary and transition periods. During a stationary period, there is no change in light transmission with respect to time and the light transmission profile can be described as a horizontal line. However, during a transition period, light transmission varies with the optical properties of the mixture and the change in light transmission through the fluid with respect to time is different from zero.

The inflection point of the transition period is defined as the transition point. The transition point occurs when the rate of change of product concentration in the mixture with respect to time is at its maximum. At this point, the second derivative is zero.

The transition time is defined as the time required to pass from 95% to 5% of the product in the mixture. The estimated transition time was based on the time between the maxima and/or minima of the derivatives. It was found that the time elapsed between the occurrences of the second derivative maximum and the first derivative maximum was proportional to the transition time.

A time delay is associated with the calculation of the first and second derivatives by the method and the use of a LOGIC scheme. The total time delay has implications on sensor placement for effective valve control or diversion of fluid flow. The developed method minimizes the time delay.

The method delivers a signal when a transition point is detected and signals the transition time. This information can be used to automate process piping valves to capture the product at the desired product concentration.

BRIEF DESCRIPTION OF THE DRAWING

The accompanying drawing illustrates several aspects of the present invention, and together with the description, serves to explain the principles of the invention. In the drawing.

Reference will now be made in detail to the present preferred embodiment of the invention, an example of which is illustrated in the accompanying drawing.

DETAILED DESCRIPTION OF THE INVENTION

Figure 1:
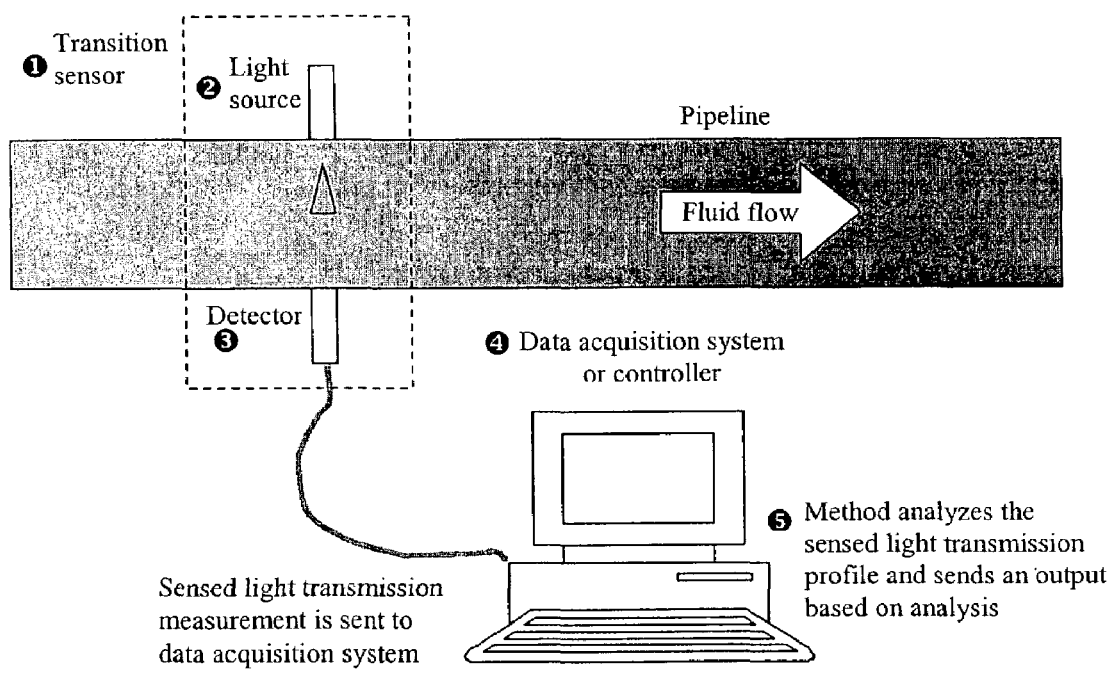
FIG. 1 is a schematic of the on-line time-based transition sensor system.

Reference is now made to the drawing FIG. 1 schematically showing the on-line time-based transition sensor system. The transition sensor 1 in transmission configuration is mounted in a piping system where multiple products of different physical or optical properties are processed. The transition sensor is composed primarily of two probes—one of which is used to direct light from a light source 2 toward the liquid product in the pipe line and the other probe is used to direct the sensed light transmission to a detector 3. The detector 3 is a photodiode or a sensor whose output is directly proportional to the amount of sensed transmitted light. The output from detector 3 is sent through a cable to a data acquisition system 4 (or some type of a controller, such as a programmable logic controller) where the method 5 generates and analyzes the sensed transmission light profile. The method 5 uses derivative analysis to determine in real-time when a transition has occurred and provides and estimate of the transition time. Once a transition has been determined and the transition time has been estimated, the data acquisition system 4 or controller sends an output (current, voltage, etc.) to signify the detected transition and the transition time to the operator, or process control equipment. The transition time may be signaled through the duration of the output signal.

Figure 2:
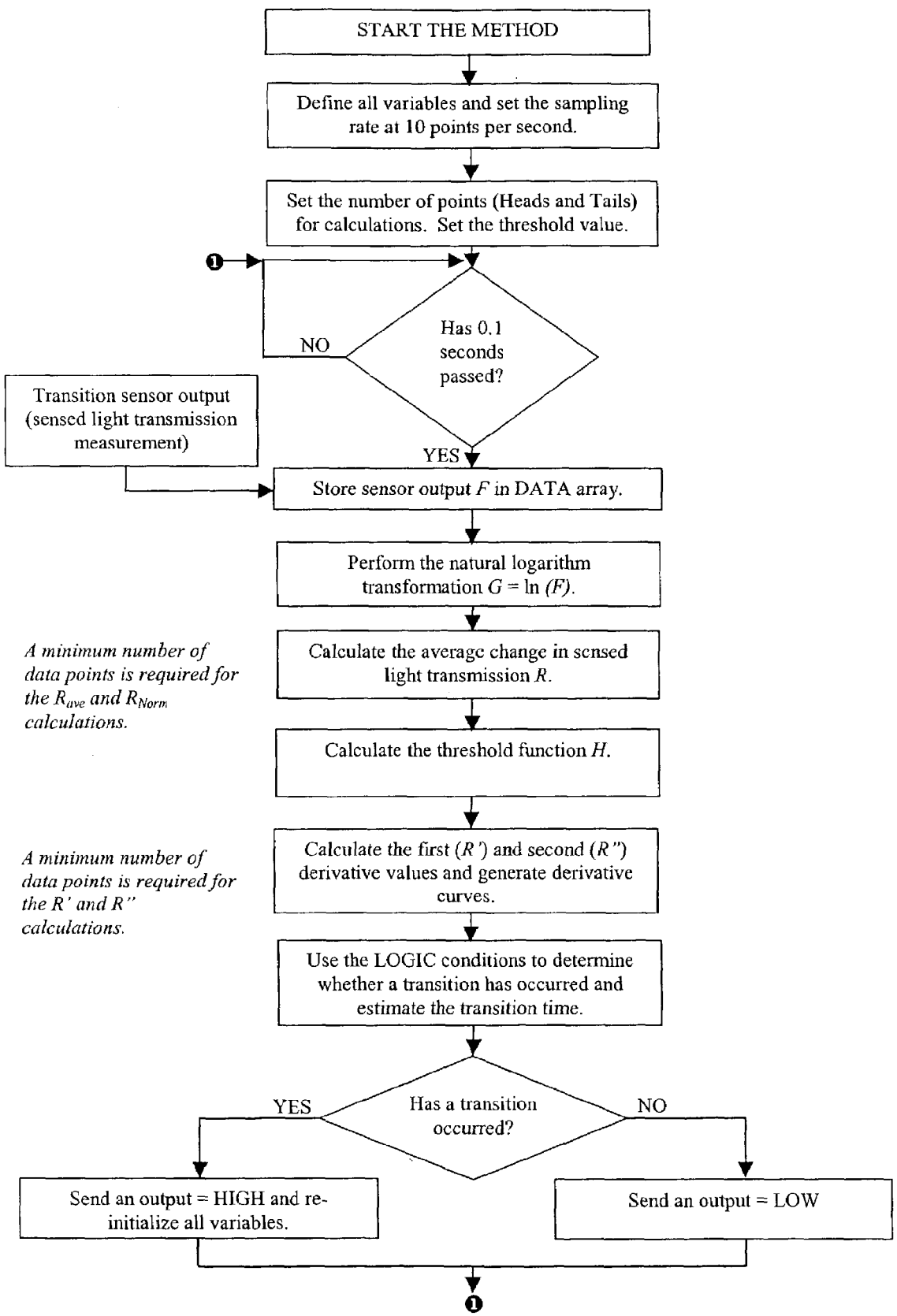
FIG. 2 is a graphic representation of the method flow chart.

Reference is now made to the drawing FIG. 2 schematically showing the method flowchart. The method is designed to operate continuously, but does have a starting point. The operating variables are initialized during the startup period. A timer paces the data collection with a data collection rate of ten points per second. The sensed light transmission measurement F is stored in the DATA array of the program. The sensed light transmission measurement F is transformed to the natural logarithm of the sensed light transmission, $G = \ln(F)$. After the required number of data points, $N_x$, to perform the averaging calculations has been collected, the method calculates the smoothened response curve R and the threshold function H. The method calculates the first (R') and second (R") derivatives after the required number of data points to perform the derivative calculations has been collected. The method uses LOGIC conditions to determine the transition point and the transition time after H has been above the threshold value for one second and when the maxima of the first and second derivatives, R' and R", have passed.

The determination of the transition point and transition time using a transmission sensor and the procedures developed that constitute the method are detailed in the following steps:

Step 1. Transmission Data, F

Figure 3A:
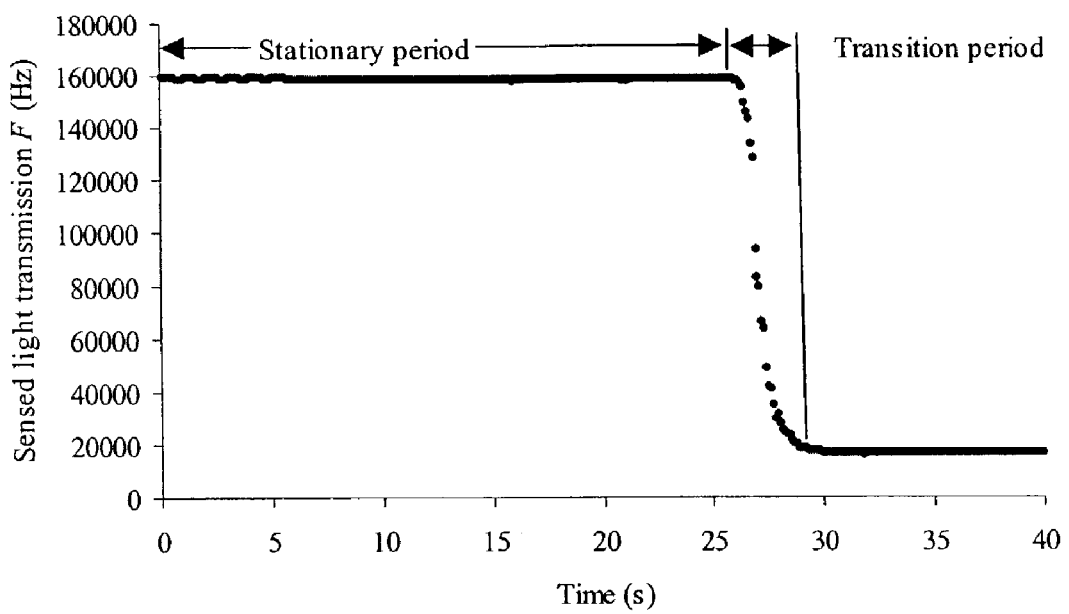
FIG. 3a is a graphic representation of a typical water-to-product transmission and FIG. 3b is a graphic representation of a typical product-to-water transition sensed light transmission profiles. The sensed transmission light, F, is measured in pulses/second (Hz). During the stationary periods (one for water, another for skim milk), the transmission profile can be described as a horizontal line. However, during the water-to-product transition, F decreases with time. Likewise, during the product-to-water transition, F increases with time. These transition curves can no longer be described as horizontal lines, and the slopes or curvatures of the transitions are either positive or negative.
Figure 3B:
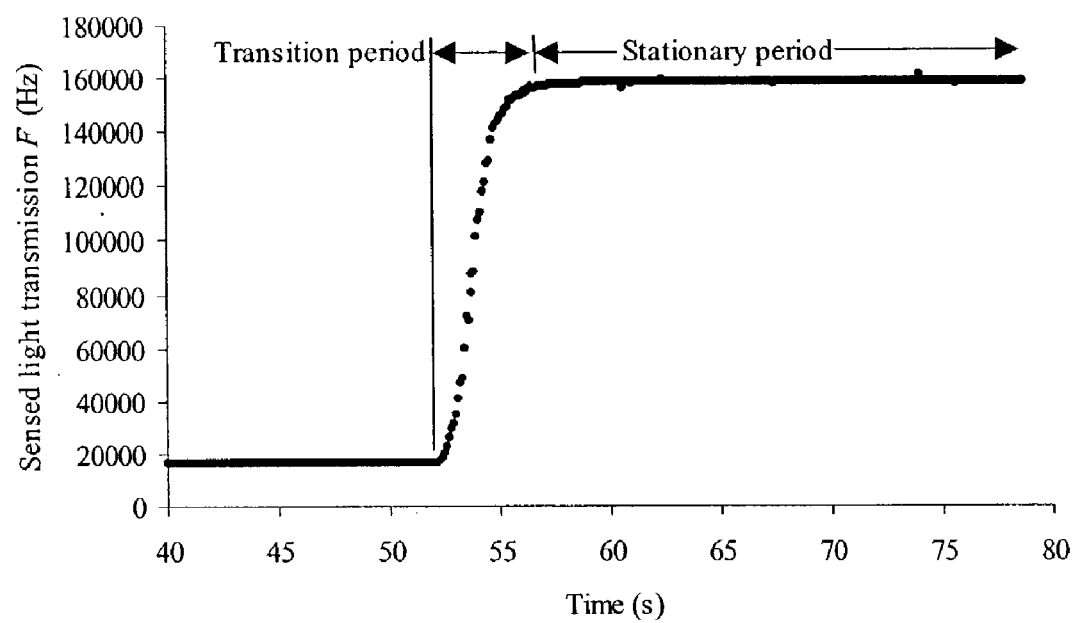

The transmission data was measured using a digital light detector that yielded a pulse signal with the pulses proportional to the light transmitted. The advantage of a pulse signal over an analog signal is the increase in operating range. FIG. 3 shows a typical transmission response profile.

Step 2. Natural Logarithm Transformation, G

Figure 4:
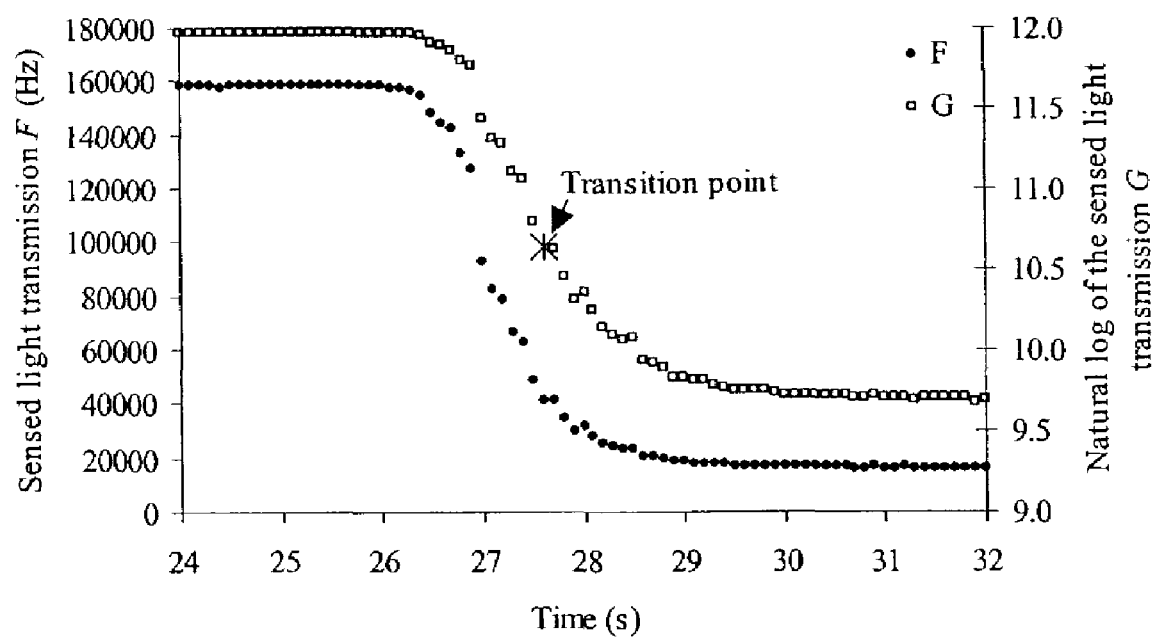
FIG. 4 is a graphic representation of the effects of the natural logarithm transformation, G=1n (F), of the measured optical response, F. The sensed light transmission profile F is transformed into G which is proportional to concentration. The inflection point of the G curve is defined as the transition point.

The extinction of light through a medium decreases exponentially as described by the exponential law of absorption (or Beer's Law). This is true for non-particulate fluids and for skim milk. However for highly scattering fluids, such as whole milk, there is a deviation from this exponential decay. Highly scattering fluids scatter according to the following equation:

$$I(r) = \frac{I_0 \exp(-\kappa r)}{r^m},$$

where I(r) is the light intensity at a distance r from the $I_0$ source, $\kappa$ is the absorption coefficient of the fluid, and m is the exponent relating light diffusion in the r direction. In either case, the concentration of the product will be more correlated to the logarithm of the signal than to the raw signal. Thus, for an optical transmission system, the measured signal F is transformed into a measurement proportional to product concentration by the natural logarithm transformation, $G = \ln(F)$. This results in a plot G as a function of time, shown in FIG. 4. The inflection point of G is defined as the transition point.

Step 3. Smoothened Response Curve, R

Figure 5A:
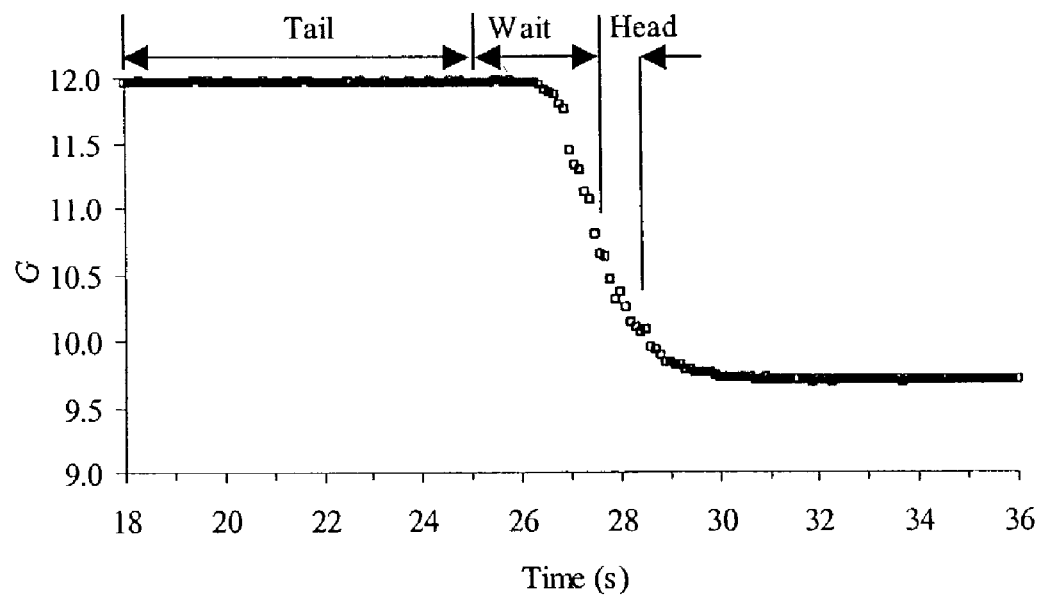
FIG. 5a is a graphic representation of a smoothing procedure to average the G profile yielding the R curve (FIG. 5b).

The optical transmission signal contains many perturbations including detector noise, EMF noise, non-homogeneity of the fluid, and fluid turbidity that distort the signal, as well as the calculated first and second derivative curves. A unique smoothing procedure was developed to smooth the data and clarify the transition period, as well as the first and second derivatives. The basic premise in developing a smoothing procedure was that a signal changes from one level to another over a period of time when the product changes. After a product transition, the signal becomes stable at a new level for a relatively extended period. The smoothing procedure was developed using three time periods: a Head, Wait, and a Tail. The Head, Wait, and Tail periods are shown graphically in FIG. 5a and are further discussed below.

Head Period

The Head period is used to smooth the curve by averaging a number of consecutive points, $N_H$, to given an average $S_H$. The number of data points in the Head must be odd and may range from a minimum of one to a maximum of the number of data points in the transition period. The first point in the Head is the current data point, n=1 and the last point, $n = N_H$. The average $S_H$ is assigned to the midpoint of the Head period. Both curve smoothing and a time delay in determining the transition point increase with $N_H$. $N_H$ was set at five points in the example and the average of the Head points, $S_H$, was calculated using the following formula:

$$S_H = \frac{1}{N_H} \sum_{i=1}^{N_H} G_i.$$

Wait Period

The Wait period contains $N_W$ data points. These points are not used in the calculation. The function of the Wait period is to separate the Head and the Tail. After a transition has passed, all of the Head points will be at the new level, while all of the Tail points will be at the previous level. The minimum number of data points in the Wait period is equal to the number of the data points contained in the transition period. NW was set at 30 points in the example.

Tail Period

The Tail period provides a reference or historical measured response level for the previous product. The average reference level, $Y_T$, is calculated by averaging $N_T$ data points beginning at the data point $N_H + N_W + 1$ and ending at $N_H + N_W + N_T + 1$. The average $S_T$ is assigned to the midpoint of the Tail period. A large odd number of data points were included in the Tail period to give it stability as a reference. The Tail period typically will contain three to four times the number of data points as contained in the transition period. $N_T$ was set at 70 points in the example and was calculated using the following formula:

$$S_T = \frac{1}{N_T} \sum_{i=N_H+N_W+1}^{N_H+N_W+N_T+1} G_i.$$

Finally, R is defined as:

$$R = |S_H - S_T|.$$

Figure 5B:
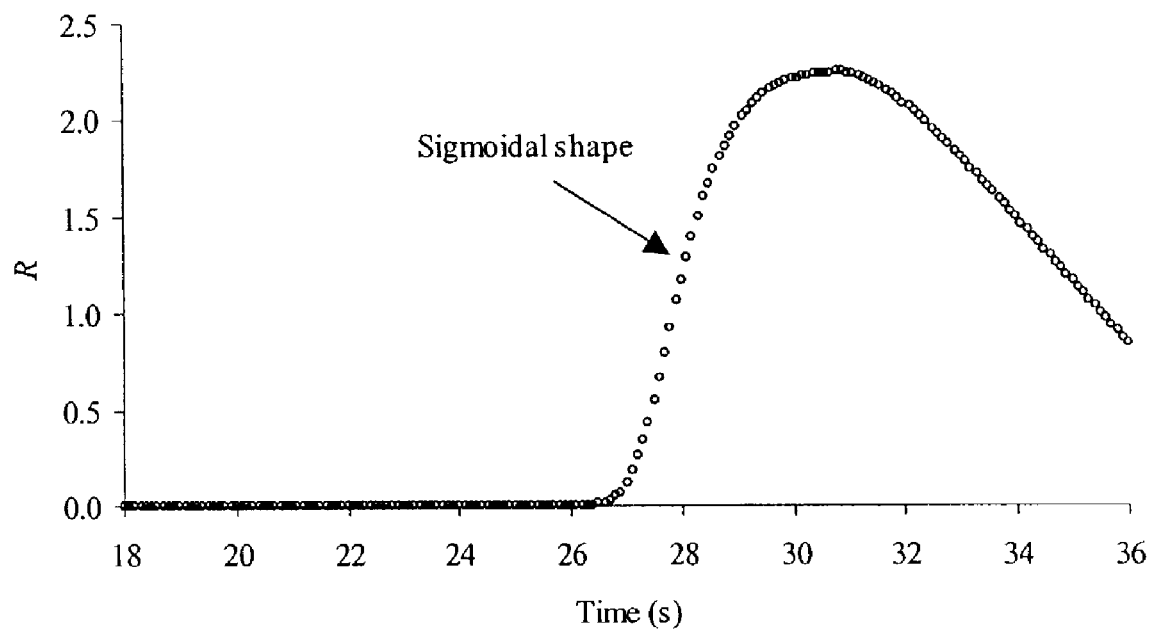
FIG. 5c shows the threshold function H and the specified threshold value, used to determine when a significant change in light transmission has occurred.

R mimics the transition period and has sufficient smoothing to permit the first and second derivatives to be calculated. The segment of R that represents the transition period is the sigmoidal section. FIG. 5b shows the sigmoidal segment for the example between 26 and 31 seconds. The use of the absolute value function assures that the values are positive for both an increasing and decreasing measured response and simplifies the LOGIC conditions.

Step 4. Threshold Function, H

Figure 5C:
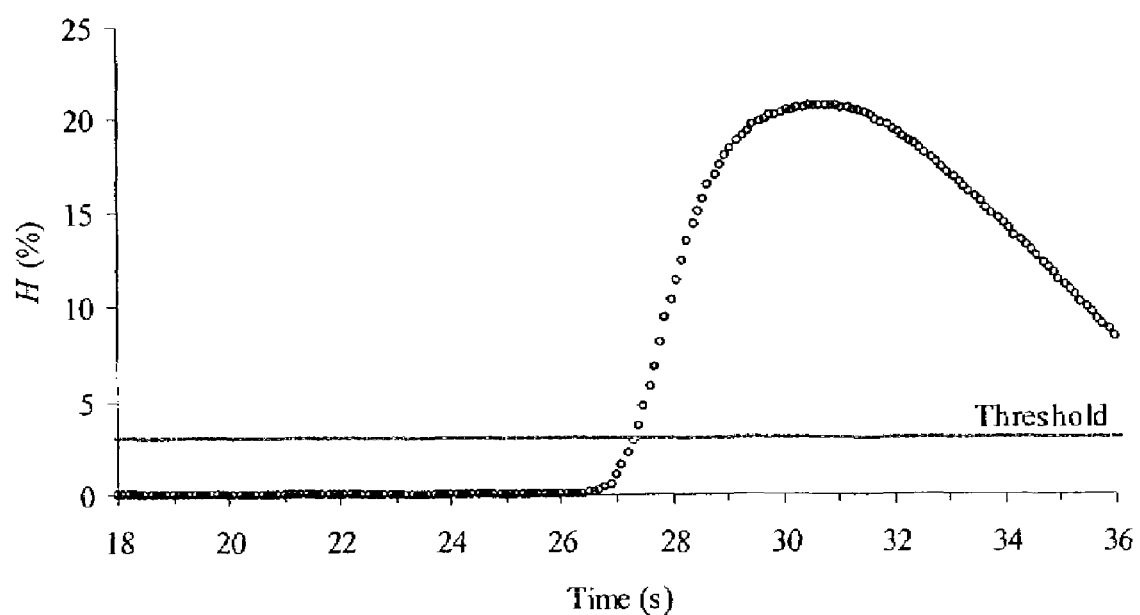

A threshold function is required to determine when a significant change has occurred, and to eliminate consideration of insignificant fluctuations resulting from electronic or fluid-related noise. A threshold function H was defined as follows:

$$H = \left| \frac{S_H - S_T}{\frac{1}{2}(S_H + S_T)} \right| \times 100\%,$$

where H is equivalent to a normalized percent change in sensed light transmission. $S_H$ and $S_T$ are as defined in Step 3. This technique was found to work for both small and large magnitudes of change in transmission response levels. A significant change in response was said to have occurred when the H curve was above the threshold value as shown in FIG. 5c. The threshold value must be selected based on the differences between optical properties of the fluids being detected. The threshold value was set at 3% in the example.

Step 5. First Derivative Function, R'

Figure 6A:
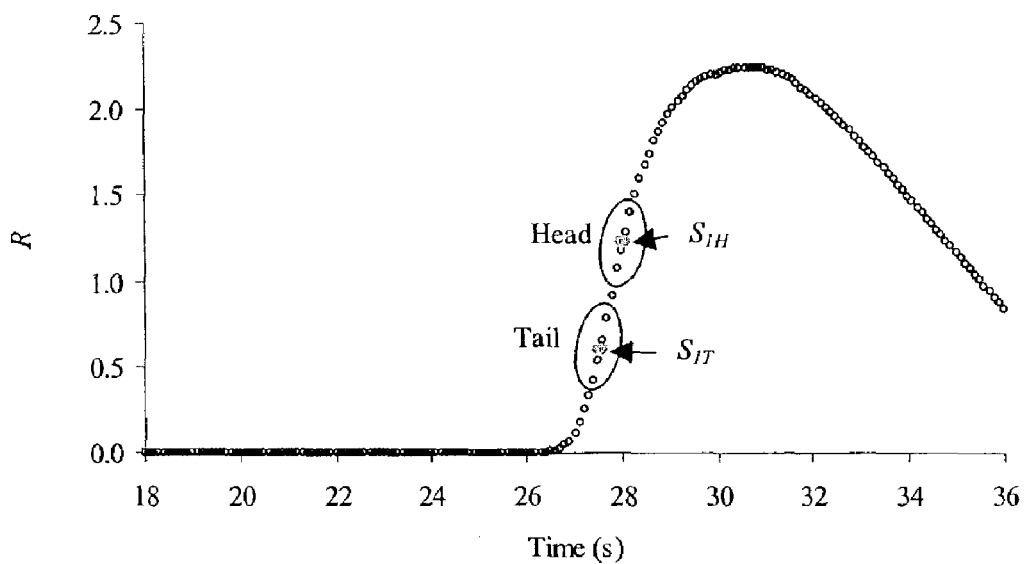
FIG. 6a is a graphic representation of the procedure used to calculate the first derivative.
Figure 6B:
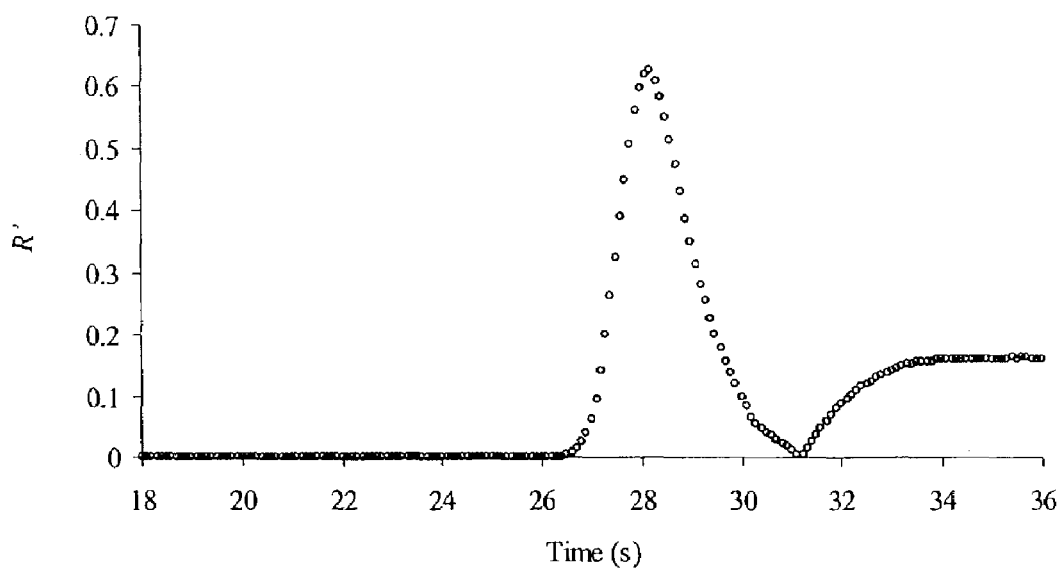
FIG. 6b shows the resulting first derivative curve, R'.

The first derivative R' of the sigmoidal section of R was calculated by taking the difference between the averages of the Head and Tail sections. The time between the respective midpoints remains constant, thus the difference is proportional to the first derivative. The first derivative was calculated as the absolute difference between the averages of the Head and Tail sections. The number of data points $N_F$ used in the first derivative calculation was odd. An equal number of points $((N_F-1)/2)$ were used in the Head and Tail sections. The calculated slope was assigned to the midpoint of $N_F$. The midpoint of $N_F$ is not used in the calculations. The example used nine data points in the first derivative calculation, and the slope was calculated as follows:

$$S_{1H} = \frac{1}{\left(\frac{N_F - 1}{2}\right)} \sum_{i=1}^{\left(\frac{N_F-1}{2}\right)} R_i$$

$$S_{1T} = \frac{1}{\left(\frac{N_F - 1}{2}\right)} \sum_{i=\left(\frac{N_F-1}{2}\right)+2}^{N_F} R_i,$$

$$R' = |S_{1H} - S_{1T}|$$

where $S_{1H}$ is the average of the most recent four R data points, and $S_{1T}$ is the average of the preceding four R data points, as shown in FIG. 6. The midpoint between the Head and Tail sections is not included in the calculation.

Step 6. Second Derivative Function, R"

Figure 7A:
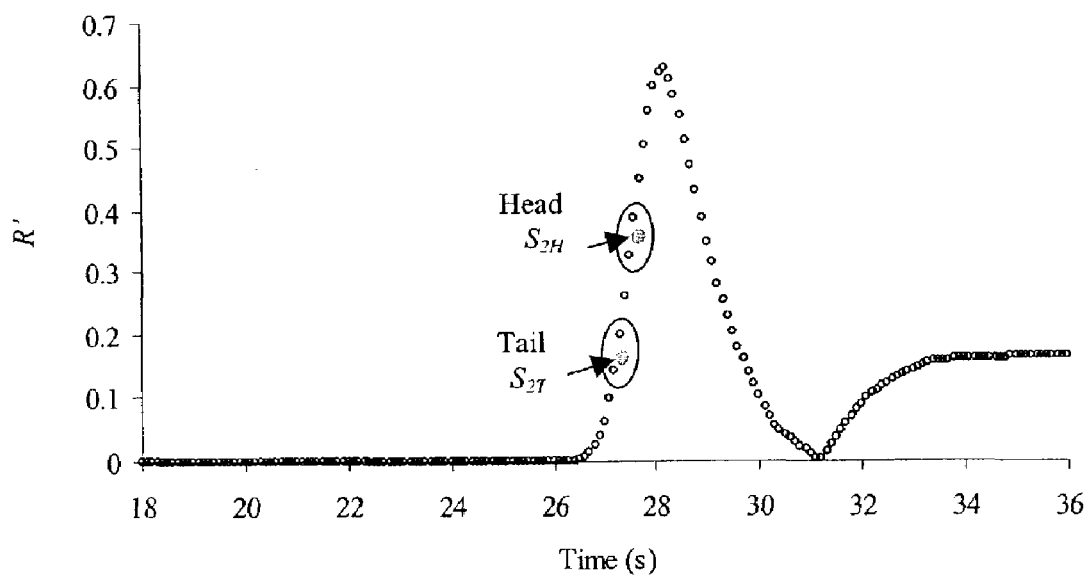
FIG. 7a is a graphic representation of the procedure used to calculate the second derivative.
Figure 7B:
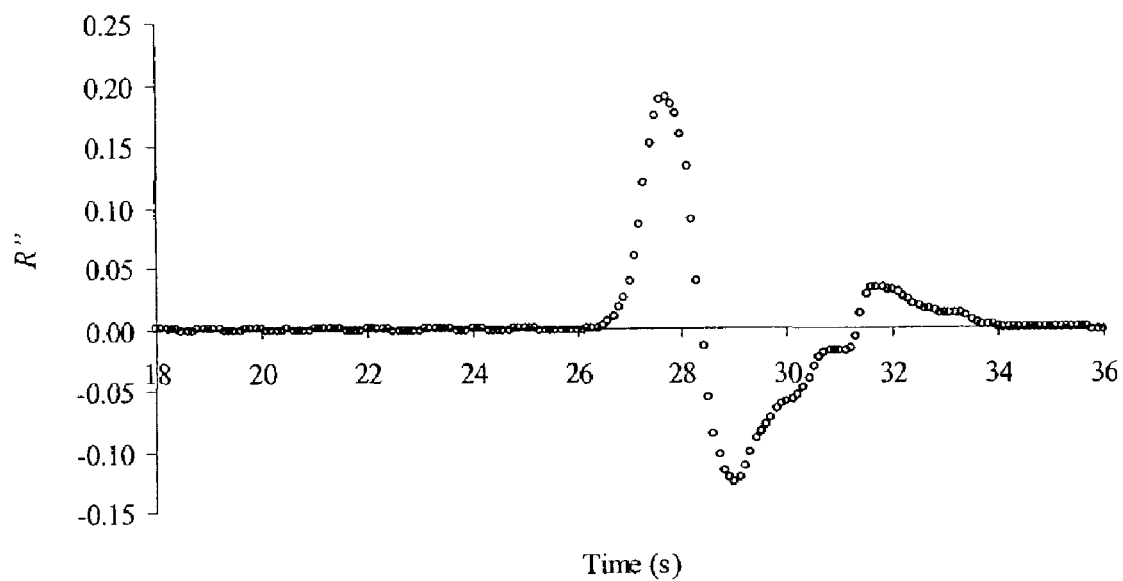
FIG. 7b shows the resulting second derivative curve, R".

The second derivative is based on the first derivative curve R' and is mathematically similar to the first derivative calculation. The total number of data points used in the second derivative calculation is $N_S$ and was an odd number. An equal number of points $((N_S-1)/2)$ are used in the Head and Tail sections. The calculated slope is assigned to the midpoint of $N_S$. The midpoint of $N_S$ is not used in the calculations. The example uses an $N_S$ of five points with the second derivative calculated as follows:

$$S_{2H} = \frac{1}{\left(\frac{N_S - 1}{2}\right)} \sum_{i=1}^{\left(\frac{N_S-1}{2}\right)} R'_i$$

$$S_{2T} = \frac{1}{\left(\frac{N_S - 1}{2}\right)} \sum_{i=\left(\frac{N_S-1}{2}\right)+2}^{N_S} R'_i,$$

$$R'' = S_{2H} - S_{2T}$$

where $S_{2H}$ is the average of the most recent two R' values, and $S_{2T}$ is the average of the preceding two R' values, as shown in FIG. 7.

Step 7. LOGIC Conditions

A transition point is located when the following conditions are met.

a. The magnitude of the threshold function H is above the threshold value for at least one-second duration, and b. Four sequential points of R' have a magnitude less than the located maximum of the first derivative curve (i.e., the peak of the first derivative curve is determined).

Once the maximum of the first derivative curve is identified, the transition point has been identified and the method may send an output signal.

The transition time can be estimated when the following condition is met.

Two subsequent points of R" are below the located maximum of the second derivative curve (i.e., the peak of the second derivative curve is determined).

Figure 8:
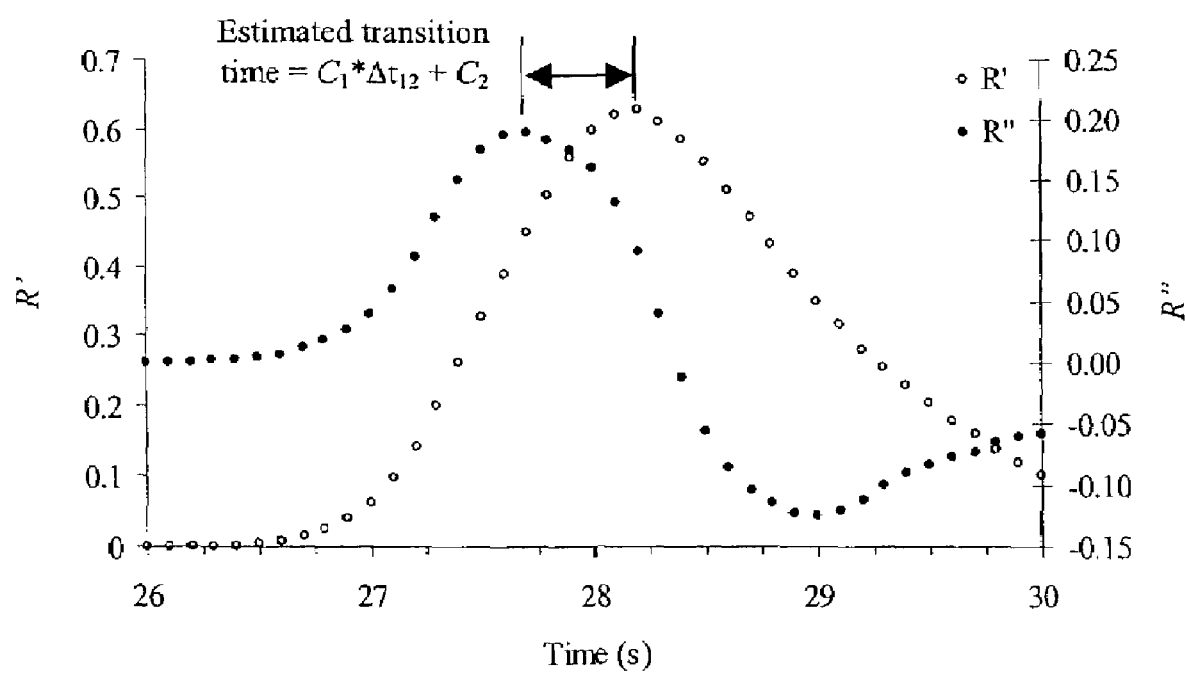
FIG. 8 is a graphic representation of the procedure used to estimate the transition time.

Once the maximum of the second derivative curve is identified, the transition time is estimated to be the time elapsed between the maxima of the first and second derivative curves multiplied by a constant. FIG. 8 shows the difference between the maxima of the derivatives.

Step 8. Method Time Delay

The total time delay for detecting the transition and providing an estimate of the transition time is equivalent to $$\Delta t_{delay}(s) = \frac{\left(\frac{N_H - 1}{2}\right) + N_F + N_D}{D_R},$$

where $\Delta t_{delay}$ is in seconds, $N_D$ is the number of data points needed to determine whether the maximum of the first derivative has passed, and $D_R$ is the number of data points collected in one second. The first term in the numerator is time delay due to the smoothing procedure; the second term is the time delay due to the first derivative procedure, while the last term is due to determining the maximum of the first derivative curve. The denominator, $D_R$, converts the total number of data points in the delay to time units. $N_D$ and $D_R$ are set at four data points and ten data points per second, respectively.

For the example, the total time delay was one second. This implied that for effective valve control, the minimum distance between the sensor and the valve to be activated must be equivalent to the process velocity multiplied by the total time delay (e.g., when fluids are processed at 1.5 meters per second, the sensor must be placed 1.5 meters upstream from the valve). As a rule of thumb, the process velocity times one second is the minimum distance value between the sensor and the valve.

The results of 78 tests designed to evaluate the response of the transition sensor system over a range of process velocities and pipe system lengths analyzed are set forth in Example 1 below.

EXAMPLE 1

Un-pasteurized skim milk was processed at pipe flow velocities of 0.91, 1.37, and 1.83 meters per second through pipe system lengths of 5.97, 15.72, and 25.48 meters. Un-pasteurized raw milk was also processed at pipe flow velocities of 1.37 and 1.52 meters per second through the same pipe system lengths stated above. These pipe flow velocities were chosen based on typical industry processing velocities.

The transition sensor was mounted in the piping system and the sensor output was sent to the data acquisition system for the method to analyze. Water-to-product transitions were simulated by allowing water at 25° C. to re-circulate through the piping system for three to five minutes. The valve on the product tank was then manually opened for twenty to forty seconds to allow the milk to chase the water out of the piping system. Similarly, product-to-water transitions were simulated once the valve on the product tank was closed and water was allowed to chase the milk out of the piping system. The sensed light transmission profiles were analyzed to determine the transition times. These measured transition times were then compared to the transition times estimated by the method.

Figure 9A:
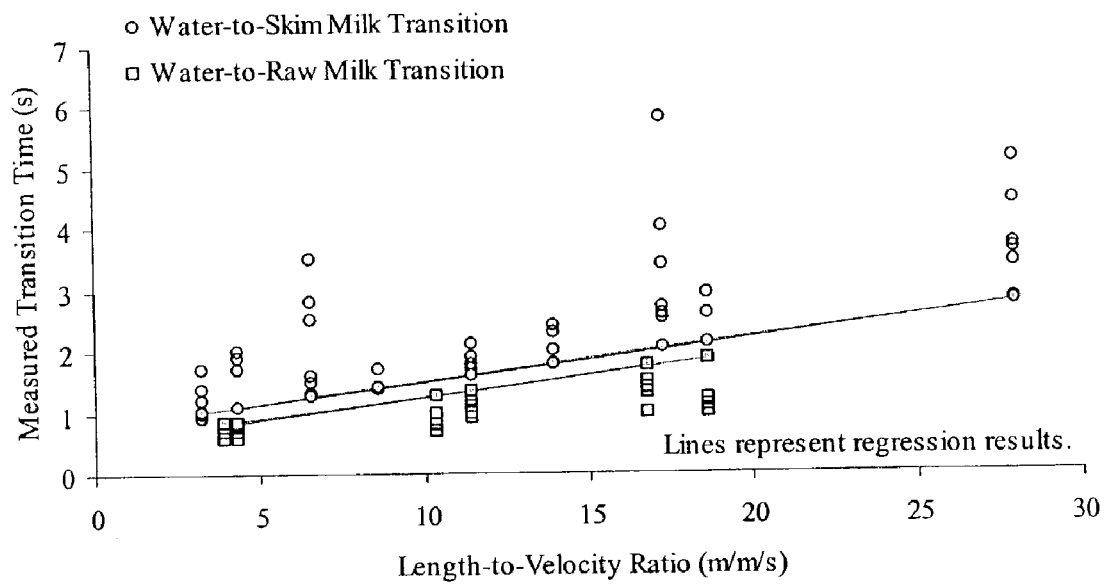
FIGS. 9a and 9b show the results of the tests conducted to determine the robustness of the method.
Figure 9B:
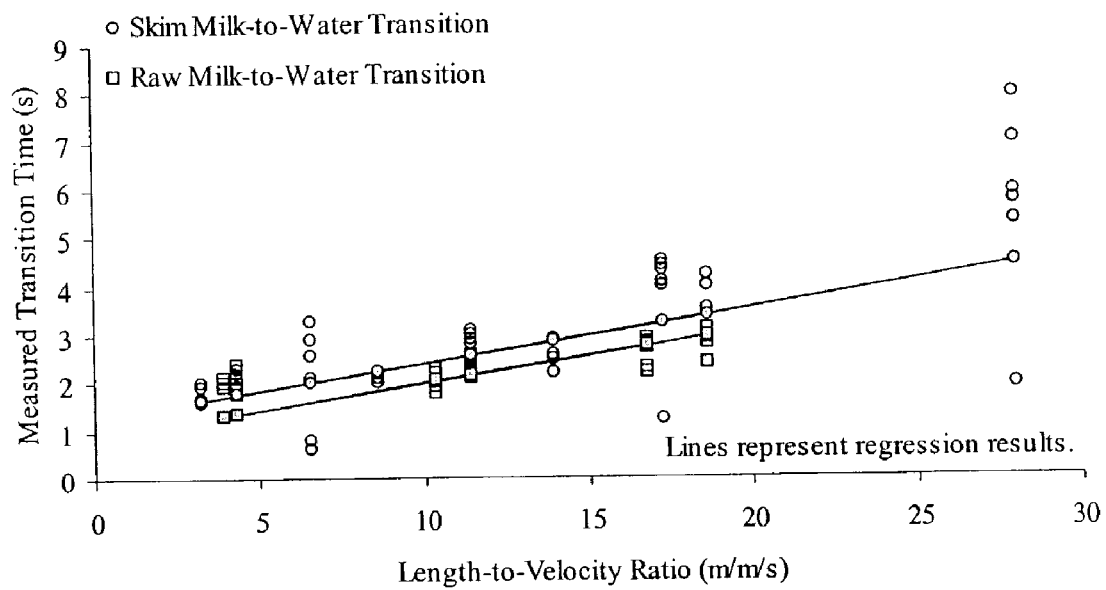

Results of the tests described in Example 1 are set forth in FIG. 9. The measured transition times were plotted against the ratio of pipe system length to pipe flow velocity. A linear regression based on the following regression model was performed:

$$t_{meas}(s) = \beta_1 \left(\frac{\rho}{\mu}\right)_{product} + \beta_2 \left(\frac{L}{v}\right),$$

where $t_{meas}$ is the measured transition time in seconds; $\rho$ and $\mu$ are the density and viscosity of the product in kilogram per cubic meter and Pascal-second, respectively; L is the pipe system length in meters; v is the pipe flow velocity in meters per second; and $\beta_1$ and $\beta_2$ are regression coefficients. The properties of the product dictate the intercept of the regression equation.

Linear regression results are as follows:

water-to-product transition:

$$t_{meas}(s) = (1.052 \times 10^{-6}) \left(\frac{\rho}{\mu}\right)_{product} + (0.071)\left(\frac{L}{v}\right), R^2 = 0.8887$$

product-to-water transition:

$$t_{meas}(s) = (1.697 \times 10^{-6}) \left(\frac{\rho}{\mu}\right)_{product} + (0.113)\left(\frac{L}{v}\right), R^2 = 0.9261$$

These equations may be used to determine the measured transition time for transitions involving water and skim milk or water and raw milk. For example, to determine the time for a water-to-skim milk transition flowing through 25 meters of piping at a process velocity of 1.5 meters per second, {PARA0}

$$t_{meas}(s) = (1.052 \times 10^{-6}) \left(\frac{1040 \ \text{kg/m}^3}{1.37 \times 10^{-3} \ \text{Pa} \cdot \text{s}}\right) + (0.071)\left(\frac{25 \ \text{m}}{5 \ \text{m/s}}\right).$$

$t_{meas}(s) = 1.15$ sec

Figure 10A:
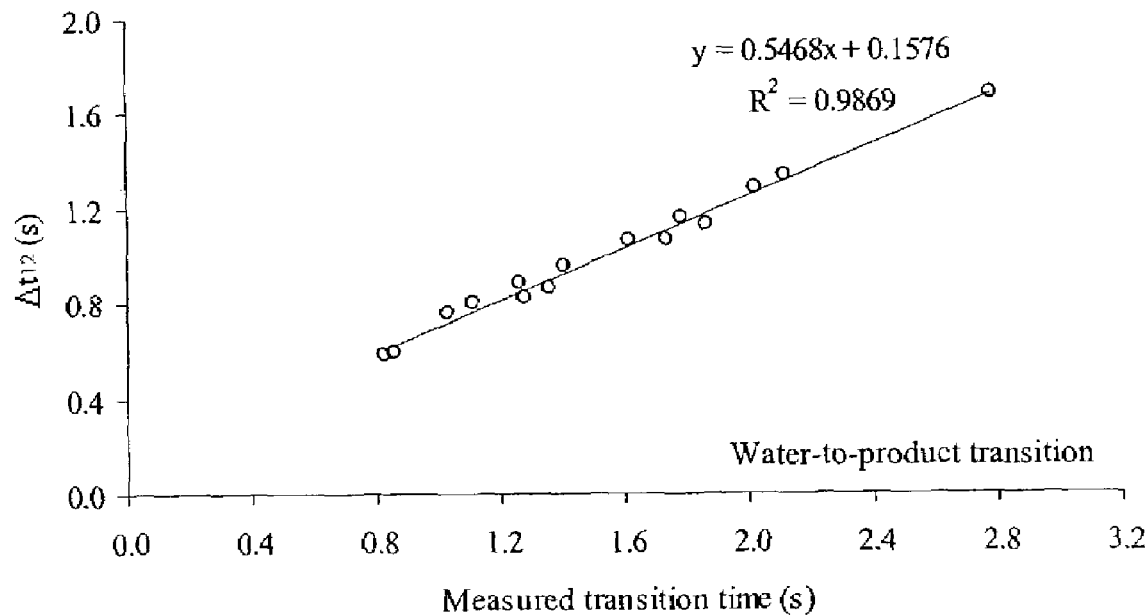
FIG. 10 shows the calibration of the elapsed time between the first and second derivative maxima to the measured transition time for water-to-product transitions (FIG. 10a) and product-to-water transitions (FIG. 10b).
Figure 10B:
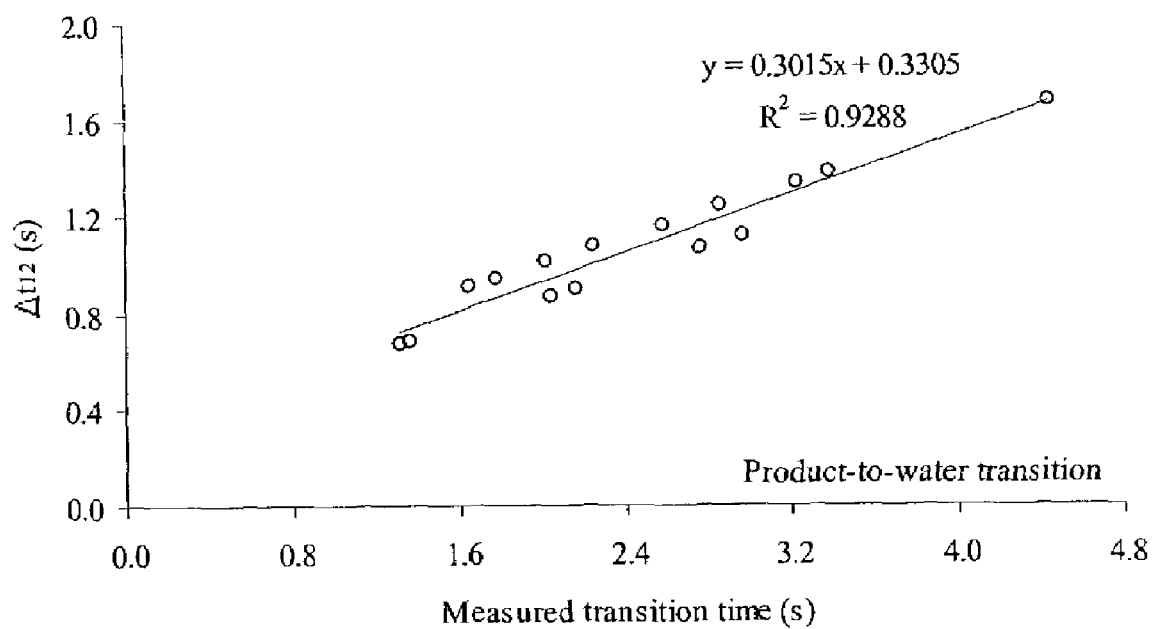

The time elapsed between the maxima of the first and second derivative curves were then calibrated against the linear regression results. This calibration is set forth in FIG. 10 and the equations are as follows:

water-to-product transition:

$\Delta t_{12}(s) = 0.5468 * t_{meas}(s) + 0.1576, R^2 = 0.9869$, product-to-water transition:

$\Delta t_{12}(s) = 0.3015 * t_{meas}(s) + 0.3305, R^2 = 0.9288$, where $\Delta t_{12}$ is the elapsed time between the maxima of the first and second derivative curves in seconds and $t_{meas}$ is the measured transition time.

Re-arranging the above equations, the equations to estimate the transition times can be obtained as:

water-to-product transition: $t_{est}(s) = \left(\frac{\Delta t_{12}(s) - 0.1576}{0.5468}\right)$, product-to-water transition: $t_{est}(s) = \left(\frac{\Delta t_{12}(s) - 0.3305}{0.3015}\right)$.

Figure 11A:
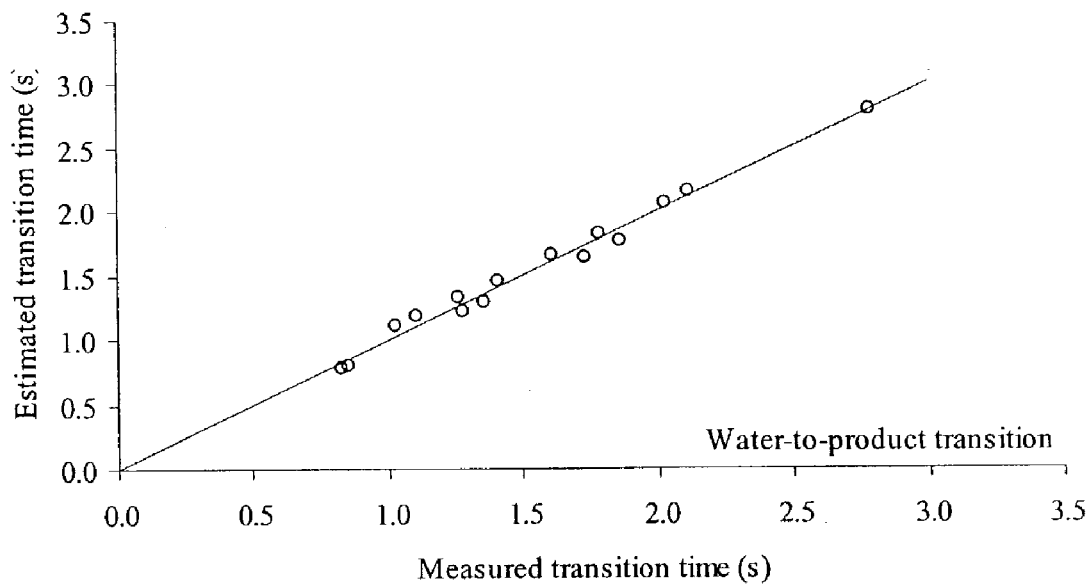
FIG. 11 shows the comparison of the estimated transition time to the measured transition time for water-to-product transitions (FIG. 11a) and product-to-water transitions (FIG. 11b).
Figure 11B:
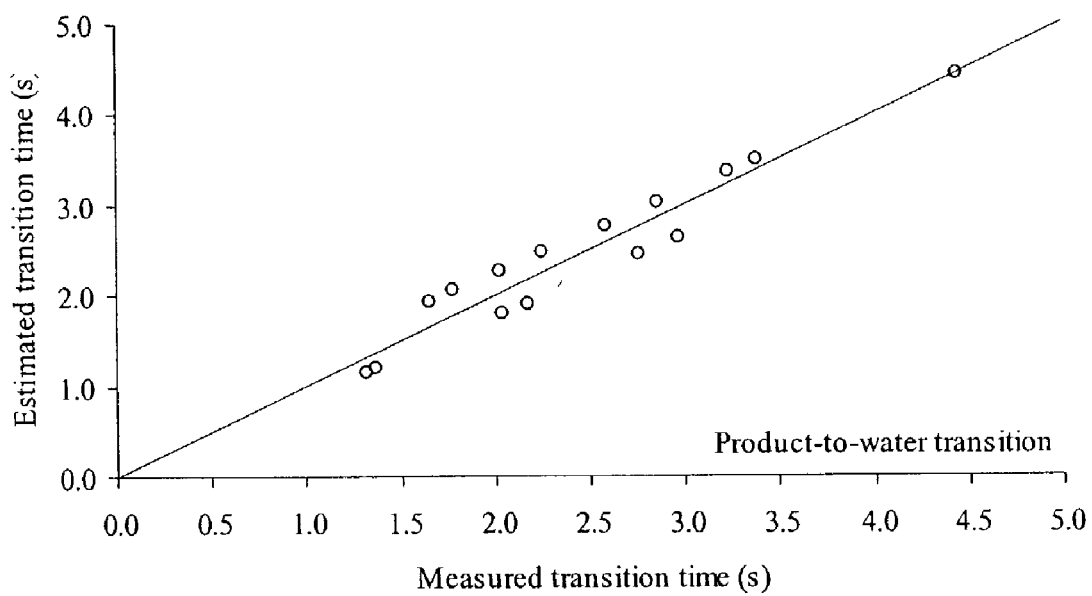

A comparison of the estimated transition times by the method to the measured transition times is set forth in FIG. 11. Hypotheses tests revealed that the slopes and intercepts of the comparison were not significantly different than unity and zero, respectively.

Suppose for a water-to-skim milk transition flowing through 25 meters of piping at a processing velocity of 5 meters per second, the method measured a 0.75 seconds elapsed time between the first and second derivative maxima. The method then estimates that the transition time is $$t_{est}(s) = \left(\frac{0.75 - 0.1576}{0.5468}\right) = 1.08 \text{ sec.}$$

Compared to the 1.15 second measured transition time given by the regression based on process conditions, there is a 6% difference between the values.

Summarizing the foregoing, the various aspects of the disclosed method for detecting product transitions include:
1. Directing light from a light source toward the liquid product in a piping system.
2. Sensing the transmission of that light through the liquid product.
3. Analyzing the sensed light transmission profile using a method based on derivative analysis.
4. Establishing a transition point and estimating the transition time.
5. Determining product transition points from measurement of an optical (or other) property of the flowing media.
6. Determining product transition time from measurement of an optical (or other) property of flowing media.
7. Optionally converting an optical transmission signal to a signal proportional or nearly proportional to product concentration by taking the logarithm of that signal.
8. Smoothing the measured signal or converted signal to form a sigmoidal curve segment that mimics the response during the transition segment. The method employs a Head, Wait, and Tail periods. The length of the Head period is preferably less than the length of the transition. The length of the Wait period is preferably equal to or greater than the length of the transition. The length of the Tail period is preferably three to four times that of the transition time. The Tail period provides a steady representation of the historic past from which comparisons are made.
9. Estimating the first derivative by subtracting curve segment averages.
10. Estimating the second derivative by subtracting curve segment averages.
11. Estimating transition time by measuring the time between the maxima of the first and second derivatives and multiplying this value by a constant and by optionally adding a constant.
12. Determining the transition point using time based signal analysis that eliminates the need for response-based calibrations.
13. Determining the transition point and transition time for multiple products without the need for calibration.
14. Other methods were tested for relating the transition time to calculated parameters in the derivative analysis including:
    a. A method that related the time between the second derivative maximum and the second derivative minimum to the transition time, and
    b. A method for relating the slope of G around the inflection point to the transition time.

These other methods are similar to the method described in this disclosure and are considered an extension this method.
15. Signaling the transition time through the duration of the output signal.

It is also possible to take the slope of the first derivative curve at the inflection point and estimate the transition time, as well as to examine the difference between the first derivative maximum and the second derivative minimum. This is another option. It is also possible to look at other curve characteristics for determining correlations between the curve parameters and transition time. In other words, other parameters from the analysis of the signal can be used to correlate to the transition time.

The foregoing description of the various embodiments of the invention is provided for purposes of illustration and description. It is not intended to be exhaustive or to limit the invention to the precise form disclosed. Obvious modifications or variations are possible in light of the above teachings. Furthermore, co-pending U.S. patent application Ser. No. 10/201,117, filed Jul. 23, 2002, is incorporated herein by reference to provide an understanding of one possible example of a transmission sensor for use in liquid product piping systems. The embodiments described provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for detecting a characteristic of a flow of a liquid in a pipe for intended use in determining a transition point among two products forming the flow, comprising:
    (a) obtaining a first signal representative of the characteristic of the flow;
    (b) transforming the first signal into a measurement proportional to the characteristic;
    (c) repeating steps (a) and (b) until a plurality of measurements are obtained;
    (d) evaluating the measurements to determine whether the flow is in a stationary stage representing the presence of only one product or a transition stage representative of the presence of two products;
    (e) when in the transition stage, continuously determining a rate of change in a selected group of the plurality of measurements including measurements obtained during the transition stage;
    (f) determining when the rate of change of the selected group is at a maximum value; and
    (g) generating a second signal indicative of the transition point when the rate of change in a predetermined number of measurements in the selected group is less than the maximum value.

2. The method of claim 1, further including continuously repeating steps (a)–(d) if the flow is in the stationary stage.

3. The method according to claim 1, further including the step of maintaining the second signal for a duration proportional to the duration of the transition stage and determining a time for substantial completion of the transition.

4. The method according to claim 1, wherein the transforming step comprises taking a natural logarithm of the first signal, whereby an improved correlation of the first signal to the characteristic is obtained.

5. The method of claim 4, wherein the evaluating step comprises calculating an average change in the plurality of measurements, and when the average change exceeds a predetermined threshold value for a predetermined period of time, proceeding to steps (e)–(g).

6. The method according to claim 5, wherein the step of calculating an average change in the plurality of measurements comprises:
   determining a first average value of a first portion of the selected group of measurements;
   determining a second average value of a second portion of the selected group of measurements taken spaced in time from the first portion of the selected group of measurements; and
   determining the average change by subtracting the first average value from the second average value to obtain a first result, taking an absolute value of the first result divided by one half of a second result comprising the first average value plus the second average value, and multiplying by one hundred.

7. The method according to claim 6, wherein the second portion of the group comprises approximately 3–4 times the number of measurements in the first portion of the group.

8. The method according to claim 6, wherein the threshold value is about 3% and the predetermined period of time is at least one second.

9. The method according to claim 4, wherein the step of determining a rate of change comprises calculating a first derivative of the measurements in the selected group.

10. The method according to claim 9, wherein the step of calculating the first derivative comprises:
    determining a first average value of a first portion of the selected group of measurements;
    determining a second average value of a second portion of the selected group of measurements taken spaced in time from the first portion of the selected group of measurements; and
    subtracting the first average value from the second average value to obtain a first result, and taking an absolute value of the first result.

11. The method according to claim 9, further including calculating the rate of change in the first derivative, determining a maximum rate of change in the first derivative, and determining point when the rate of change in the first derivative is less than the maximum rate of change in the first derivative for a predetermined number of values.

12. The method according to claim 11, further including estimating a transition time by measuring the time elapsed between the maximum rate of change in the selected group and the maximum rate of change in the first derivative.

13. The method according to claim 9, further including defining a first curve representative of the first derivative, calculating a rate of change in the first derivative to define a second curve, and estimating a transition time based on a difference or time from a first selected point to a second selected point on a selected one of said curves.

14. The method according to claim 1, further including:
    determining a total time delay for detecting the transition point, and
    positioning a detector for generating the first signal at a location sufficient to allow for an adjustment in a position of a valve associated with the pipe substantially adjacent the transition point.

15. The method according to claim 1, wherein the characteristic of the flow is light transmissivity and the obtaining step comprises placing a light source and corresponding light detector in a transmission configuration adjacent to the flow.

16. A computer-readable medium having computer-executable instructions for performing the steps of claim 1.

17. A method of detecting a transition point in a characteristic of a flow of a liquid in a pipe for intended use in distinguishing among two products forming the flow, comprising:
    (a) using a detector to obtain a first signal representative of the characteristic of the flow;
    (b) detecting the transition point based on the first signal;
    (c) determining a total time delay for detecting the transition point; and
    (d) positioning the detector at a location upstream of a valve associated with the pipe at a location sufficient to allow for an adjustment in the position of the valve adjacent the transition point based on the total time delay for detecting the transition point.

18. The method according to claim 17, wherein the step of using the detector comprises placing a light source and corresponding light detector in a transmission configuration adjacent to the flow such that the first signal is representative of the light transmissivity of the flow.

19. The method according to claim 17, wherein the step of detecting the transition point based on the first signal comprises:
    (1) transforming the first signal into a measurement proportional to the characteristic;
    (2) repeating step (1) until a plurality of measurements are obtained;
    (3) evaluating the measurements to determine whether the flow is in a stationary stage representative of the presence of a first product only in the flow or a transition stage representative of the presence of two products;
    (4) when in a transition stage, continuously determining a rate of change in a selected group of the plurality of measurements including measurements obtained during the transition stage;
    (5) determining when the rate of change of the selected group is at a maximum value; and
    (6) generating a second signal indicative of the transition point when the rate of change in a predetermined number of measurements in the selected group is less than the maximum value.

20. In a system including a flow of a liquid in a pipe, a device for intended use in determining a transition among two products forming the flow, comprising:
    means for detecting a characteristic of the flow and generating a first signal representative of the characteristic; and
    computer-operated means for determining a transition point based on the first signal.

21. The system according to claim 20, wherein the determining means comprises a computer-readable medium having computer-executable instructions for performing the steps of:
    (a) obtaining a first signal representative of the characteristic of the flow;
    (b) transforming the first signal into a measurement proportional to the characteristic;
    (c) repeating steps (a) and (b) until a plurality of measurements are obtained;
    (d) evaluating the measurements to determine whether the flow is in a stationary stage representing the presence of only one product or a transition stage representative of the presence of two products;

(e) when in the transition stage, determining a rate of change in a selected group of the plurality of measurements including measurements obtained during the transition stage;

(f) determining when the rate of change of the selected group is at a maximum value; and (g) generating a second signal indicative of the transition point when the rate of change in a predetermined number of measurements in the selected group is less than the maximum value.

22. The device according to claim 20, wherein the characteristic of the flow is light transmissivity and the detecting means comprises a light source and corresponding light detector oriented in a transmission configuration adjacent to the flow.

23. A method for detecting a characteristic of a flow of a liquid in a pipe for intended use in determining a transition among two products forming the flow, comprising:

(a) obtaining a first signal representative of the characteristic of the flow;

(b) determining when a substantial change in the characteristic is occurring; and (c) determining a transition time for the substantial completion of the transition based on a parameter of the first signal.

24. The method of claim 23, further including the steps of:

(d) transforming the first signal into a measurement proportional to the characteristic;

(e) repeating steps (a) and (d) until a plurality of measurements are obtained;

and the determining when the substantial change is occurring includes:

(f) evaluating the measurements to determine whether the flow is in a stationary stage representing the presence of only one product or a transition stage representative of the presence of two products;

(g) when in the transition stage, continuously determining a rate of change in a selected group of the plurality of measurements including measurements obtained during the transition stage; and (h) determining when the rate of change of the selected group is at a maximum or minimum value.

25. The method of claim 24, wherein the rate of change corresponds to a first derivative, a second rate of change in the first derivative corresponds to a second derivative having a minimum value, and the transition time is determined based the difference in time between the maximum value of the first derivative and the minimum value of the second derivative.

26. The method of claim 23, wherein the step of determining the transition time for the substantial completion of the change includes determining the time from when the change is 5% complete to the time when the change is 95% complete.

* * * * *

UNITED STATES PATENT AND TRADEMARK OFFICE
CERTIFICATE OF CORRECTION

PATENT NO. : 6,970,248 B1
DATED : November 29, 2005
INVENTOR(S) : Payne et al.

It is certified that error appears in the above-identified patent and that said Letters Patent is hereby corrected as shown below:

<u>Title page,</u>
Item [75], Inventors, replace "Mary-Grace D. Danao" with
-- Mary-Grace C. Danao --.

Signed and Sealed this

Twenty-first Day of February, 2006

JON W. DUDAS
*Director of the United States Patent and Trademark Office*